(12) United States Patent
Guay et al.

(10) Patent No.: US 6,475,553 B2
(45) Date of Patent: Nov. 5, 2002

(54) METHOD OF MANUFACTURING A TEXTURED TOOTHBRUSH BRISTLE

(75) Inventors: Gordon G. Guay, Chelmsford, MA (US); Ahmet Cem Firatli, Wiesbaden (DE); Norbert Schaefer, Frankfurt (DE); Armin Schwarz-Hartmann, Wendelsheim (DE); Georges Driesen, Weilrod (DE); Rainer Hans, Waldems (DE)

(73) Assignee: Gillette Canada Company, Halifax (CA)

( * ) Notice: Subject to any disclaimer, the term of this patent is extended or adjusted under 35 U.S.C. 154(b) by 0 days.

(21) Appl. No.: 09/828,909

(22) Filed: Apr. 10, 2001

(65) Prior Publication Data

US 2001/0038914 A1 Nov. 8, 2001

Related U.S. Application Data

(63) Continuation of application No. 09/113,623, filed on Jul. 10, 1998, now abandoned.

(51) Int. Cl.$^7$ ................................................ B05D 1/04
(52) U.S. Cl. ...................... 427/2.29; 427/462; 427/307; 427/316
(58) Field of Search ...................... 427/2.29, 462–465, 427/200, 206, 307, 316, 322, 335, 336

(56) References Cited

U.S. PATENT DOCUMENTS

| | | |
|---|---|---|
| 2,527,501 A | 10/1950 | Saks |
| 2,704,725 A | 3/1955 | Berglund |
| 2,768,903 A | 10/1956 | Schick |
| 2,948,634 A | 8/1960 | Furendal et al. |
| 3,697,238 A | 10/1972 | Brown et al. |
| 3,698,405 A | 10/1972 | Walker |
| 3,743,557 A | 7/1973 | Grohmann et al. |
| 3,775,233 A | 11/1973 | Malge |
| 3,889,034 A | 6/1975 | Lenards et al. |
| 3,922,410 A | 11/1975 | Halloran |
| 3,968,283 A | 7/1976 | Schutte |
| 4,025,678 A | 5/1977 | Frank |
| 4,034,135 A | 7/1977 | Gregorian et al. |
| 4,138,517 A | 2/1979 | Gardner |
| 4,232,058 A | 11/1980 | Dow et al. |
| 4,246,294 A | 1/1981 | Jordan |
| 4,246,308 A | 1/1981 | Walsh |
| 4,483,893 A | 11/1984 | Harrold |
| 4,486,915 A | 12/1984 | Stewart et al. |
| 4,532,153 A | 7/1985 | Solc |
| 4,622,235 A | 11/1986 | Goerens |
| 4,671,980 A | 6/1987 | Goerens |
| 4,829,621 A | 5/1989 | Phenegar |
| 4,922,936 A | * 5/1990 | Buzzi et al. |
| 4,936,633 A | 6/1990 | Weihrauch |
| 4,958,402 A | * 9/1990 | Weihrauch |
| 5,340,200 A | 8/1994 | Erickson |
| 5,458,915 A | 10/1995 | Yamamoto et al. |
| 5,693,360 A | 12/1997 | Stern et al. |
| 5,964,508 A | 10/1999 | Maurer |

FOREIGN PATENT DOCUMENTS

| | | |
|---|---|---|
| WO | WO 86/01984 | 4/1986 |

* cited by examiner

*Primary Examiner*—Fred J. Parker
(74) *Attorney, Agent, or Firm*—Fish & Richardson P.C.

(57) ABSTRACT

The invention is based on the discovery that flocked or textured materials (e.g., for use as dental floss, or toothbrush bristles) can be manufactured without using adhesives to secure the short fibers or texture particles to the base material, or substrate. The flocked or textured materials are formed by thermally or chemically softening a preformed substrate (e.g., sheets, fibers, or filaments made of TEFLON® fibers, KEVLAR® fibers, cotton, polyester, polyethylene, or other plastic), then treating the softened substrate with short fibers or texture particles. Alternatively, the short fibers or texture particles can be applied during the formation of the substrate (e.g., in an extrusion, melt-blowing, die casting, weaving, or drawing process).

12 Claims, 2 Drawing Sheets

METHOD OF MANUFACTURING A TEXTURED TOOTHBRUSH BRISTLE

This is a continuation of U.S. patent application Ser. No. 09/113,623, filed on Jul. 10, 1998, abandoned.

FIELD OF THE INVENTION

This invention relates to short fiber or particle textured articles.

BACKGROUND OF THE INVENTION

Materials textured with short fibers or texture particles on their surfaces are used as, for example, dental hygiene articles (e.g., toothbrushes, dental floss, interdental brushes) and abrasives (e.g., manicure or pedicure products, cleaning products). Currently, the short fibers or texture particles are ordinarily attached to a surface using an adhesive.

SUMMARY OF THE INVENTION

The invention is based on the discovery that textured surfaces (e.g., for use as dental floss, or toothbrush bristles) can be manufactured without using adhesives to secure the short fibers or texture particles to the base material, or substrate. The textured materials are formed by thermally or chemically softening a preformed substrate (e.g., sheets, fibers, or filaments made of nylon, TEFLON® fibers, KEVLAR® fibers, cotton, polyester, polyethylene, or other plastic), then an electrostatic applicator is used to apply short fibers or texture particles to the softened substrate. Alternatively, the short fibers or texture particles can be applied during the formation of the substrate (e.g., in an extrusion, melt-blowing, die casting, weaving, or drawing process).

In general, the invention features a methods for manufacturing a textured article. The article can be, for example, a dental hygiene product (e.g., an oral brush bristle, a dental floss filament). The method includes the steps of contacting texture particles (or an end of short fibers having two ends) and a surface of a substrate under conditions in which a part of either the texture particles (or short fibers), the substrate, or both are softened (e.g., by treatment with a solvent or by heating); and hardening the softened part to produce the textured article.

The contacting step in the above methods can occur, for examples after extrusion of the substrate but prior to the cooling of the substrate in a heat extrusion process that includes an extrusion step and a cooling step.

The methods that include the use of short fibers can also include the step of supplying an electromagnetic field, which can cause the short fibers to align at a substantially fixed angle relative to the surface of the substrate. The short fibers can, for example, be coated with an electrically conductive material (e.g., tannic acid and starch).

The articles made by the methods described above are also contemplated as an aspect of the invention, as are toothbrushes and interdental brushes including bristles made by the above methods and dental flosses including filaments made by the above methods. Such articles can also include an active ingredient, possibly mixed with a water soluble material such as starch, pectin, or cellulose.

A different embodiment of the invention features another method for manufacturing a textured article. The method includes the steps of extruding a bilayer substrate, in which an outer layer includes short fibers; and providing an electromagnetic field prior to cooling the substrate, causing the short fibers to align at a substantially fixed angle relative to the surface of the substrate, to produce the textured article.

The substrate can be, for example, a coaxial filament having a sheath/core arrangement, where the first layer is the sheath, and the second layer is the core.

Still another embodiment of the invention also features a method for manufacturing a textured article. This method includes the steps of spraying a suspension that includes short fibers onto the surface of a substrate; and then providing an electromagnetic field, causing the short fibers to align at a substantially fixed angle relative to the surface of the substrate, to produce the textured article.

The suspension can include, for example, a polymer dissolved in a solvent, in which case the method also includes the step of removing the solvent to cause the short fibers to become fixed in the polymer at the fixed angle. Alternatively, the suspension can include a molten polymer; and the method further comprises cooling the polymer to cause the short fibers to become fixed in the polymer at said angle.

Still another embodiment of the invention features an oral brush (e.g., a toothbrush or interdental brush) including a bristle that has short fibers attached without requiring an adhesive.

Yet another embodiment of the invention features dental floss including a filament that has short fibers attached without requiring an adhesive.

The short fibers can be attached to the bristle of the oral brush, for example, or the filament of the dental floss, by thermally or chemically softening an end of the short fibers, then contacting the bristle or filament with the softened end of the short fibers. Alternatively, the short fibers can be attached to the bristle or filament by thermally or chemically softening a surface of the bristle or filament, then contacting the softened bristle or filament with the short fibers. In another alternative, the short fibers can be attached to the bristle or filament by extruding a coaxial bristle or filament, where the outside layer contains short fibers having a net dipole, and then providing an electromagnetic field prior to cooling, causing the short fibers to align at a substantially fixed angle relative to the surface of the bristle or filament. Optionally, the short fibers can include an active ingredient.

Advantages of the new articles and methods include improved mechanical properties, enhanced biocompatibility, increased control over the physical configuration of the products, and the potential for use as a reservoir for release of therapeutics in a free or controlled release (i.e., particle) form.

Short fibers or particles are attached to the substrate by a melting or dissolving process; thus, the use of toxic adhesives can be avoided.

Another advantage follows-from avoiding the use of adhesives: in general, the new methods result in a stronger attachment of the short fibers to a substrate, relative to adhesive-based methods; in some cases, the attachment is permanent. Thus, the new methods can yield products having greater mechanical integrity.

Because electrostatically charged particles or short fibers can be aligned by an electromagnetic field, the angle at which such fibers are fixed to the substrate can be precisely controlled.

Toothbrush filaments textured with short fibers or particles can penetrate deeper into interdental regions during brushing; such filaments can be constructed with smaller diameter than traditional toothbrush filaments, yet can nonetheless exhibit excellent mechanical integrity and bend recovery.

Textured dental floss can also provide a larger surface area for cleaning while flossing.

Other features and advantages of the new articles and methods will be apparent from the following detailed description, and from the claims.

DETAILED DESCRIPTION OF THE INVENTION

General

Figure 1:
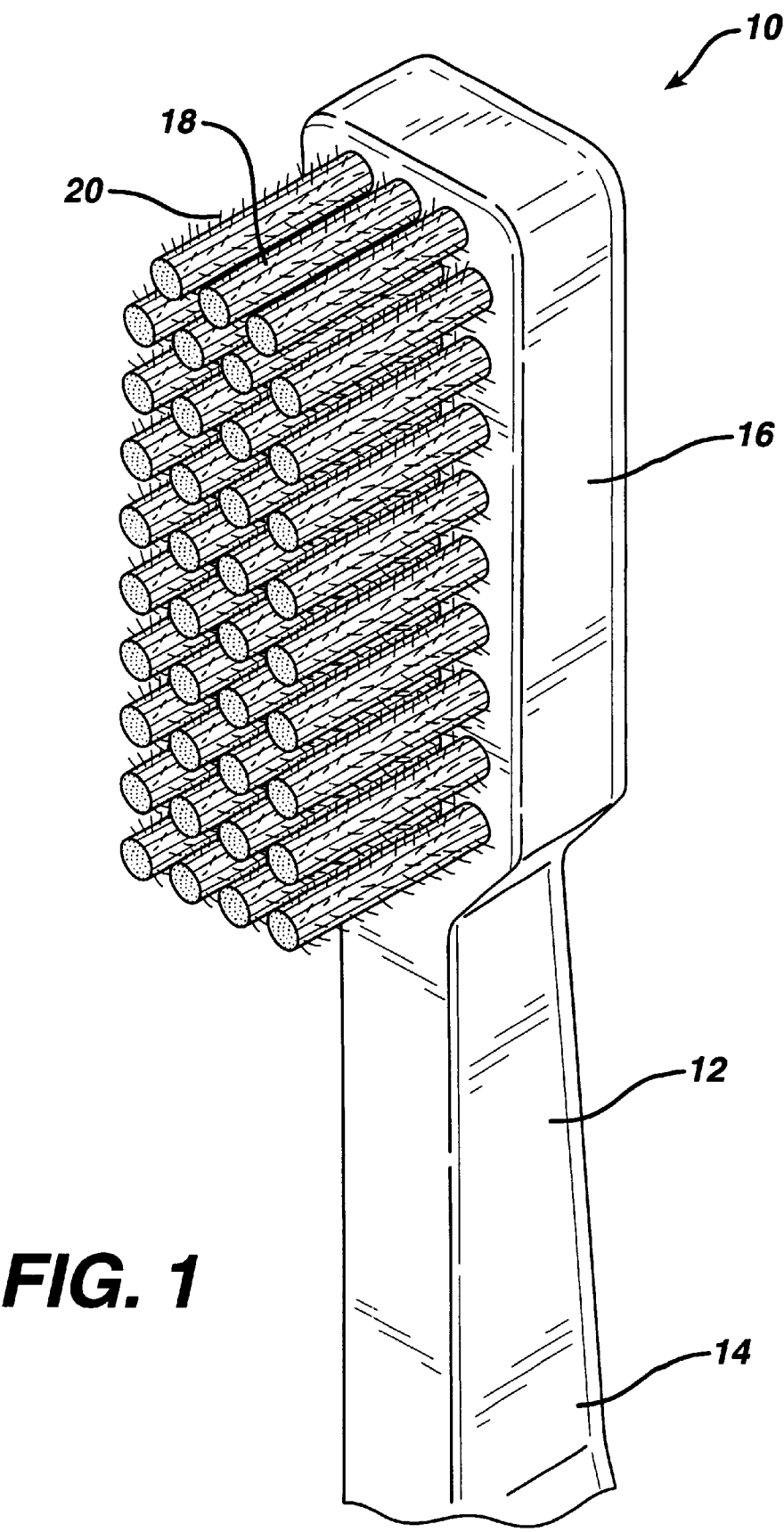
FIG. 1 is a perspective view of a toothbrush.

The substrate used for surface texturization can be made of any natural or synthetic material, provided that at least one component can be softened by heating or chemical methods. Examples of suitable materials include, but are not limited to, starch, polyolefins (e.g., polyethylene and polypropylene), polyamides (e.g., nylon 6–12, nylon 6, polyphthalamide), cotton, KEVLAR® fibers, NPBT, acetal resins, polyesters (e.g., PET, PBT), fluoropolymers (e.g., PVdF, PTFE), polyacrylates, polysulfones, and mixtures thereof. Other suitable polymeric materials include thermoplastic elastomers such as polyetheramides (e.g., PEBAX® polyetheramide materials), polyurethanes (e.g., PELLETHANE® polymers), polyolefin elastomers (e.g., SANTOPRENE® elastomers), styrene-ethylene-butylene-styrene block copolymers, styrene-butadiene-styrene block copolymers, styrene-isoprene-styrene block copolymers (e.g., KRATON® rubbers), and combinations thereof. These polymeric materials may contain fillers and additives to provide strength, lubricity, texture, abrasiveness, and color to the bristles. Examples of suitable fillers and additives include, kaolin, PTFE, titanium dioxide, and the like.

Short fibers or texture particles generally are compounded with one or more of the natural or synthetic materials above, particles or fibers possessing a net electric or magnetic dipole. Magnetic dipoles can be produced by compounding various types of fiber grade plastic resins with magnetic material such as iron oxides, samarium cobalt, or neodymium, using compounding machinery such as a twin screw extruder. The percentage of the magnetic material included in the fibers or particles is typically about 1 to 20% by weight. The pelletized compound can be extruded to produce very small fibers (i.e., about 0.004" to 0.1" in diameter and cut to 0.03" to 0.25" lengths).

Texturized components can be added with a resin and blended to form a single phase. Alternatively, separate phases can be coextruded in various configurations, e.g., a trilocular (i.e., a three lumen) bristle with a central spine of one material and an outer annular wall of another material, with one polymer forming a sheath surrounding another polymer (sheath/core), with one polymer forming a coating over a sheet of another polymer, or polymers in a side-by-side configuration. The components can also include multi-core fiber (e.g., for use as dental floss), individual fibers surrounded by a sheath (e.g., dental floss, bristles for oral brushes), sheets (e.g., membranes or upholstery materials), or combinations thereof.

An electromagnetic field or current can be used to direct the short fibers or texture particles to the molten surface of the substrate. In the manufacture of textured articles, the field or current can also be used to orient all of the fibers at a particular angle. An electrostatic field, for example, can result in the short fibers being aligned perpendicular to the surface of the substrate. For magnetism-based orientation, base material selection requires melt temperatures to be below the temperatures at which magnetic properties are lost.

The short fibers or texture particles can be attached in a regular pattern (e.g., evenly spaced along each dimension of the substrate, arranged in a geometrical pattern, or arranged in the shapes of numbers, letters of the alphabet, or other ornamental designs) or randomly distributed. Such patterns can be made, for example, by discretely softening an area of the substrate, or by using a stencil, screen, or other masking method to allow short fibers or particles to selectively penetrate a particular area of the softened substrate. The fibers or particles can also be arranged in a spiral pattern along the length of a filament, or arranged in two single lines on opposite sides of a filament.

Since the surface texturization is not necessarily required for the structural integrity of the main fiber, specialty fibers can be used to provide an added functionality to a toothbrush or floss filament. Examples of unique fibers which can be incorporated into the filaments include super-absorbent fibers, abrasive fibers, and slippery fibers. Any type of fiber capable of being produced can be used as a short fiber for surface texturization. These short fibers can vary in length and denier. The range of fiber lengths suitable for electrostatic coating ranges from 0.03" to 0.25". In addition, numerous types of materials in particle form can be applied including various types of micronized abrasives, TEFLON® fibers, and salts. The invention is also not limited to the application of these materials to fiber surfaces; it is also applicable to surfaces including foams, plastics, metals, and wood.

Therapeutics

The substrate, short fibers, and/or texture particles can be treated with a medicament or other active ingredient. Alternatively, the short fibers or texture particles can be made of a biodegradable or water-soluble material with an active ingredient dissolved therein. Fibers or particles can be made of starch, for example.

Many different substances, singly or in any suitable combination, can be used as active ingredients. For use in dental hygiene articles, the substances or combinations of substances must be acceptable for use in the mouth (e.g., non-toxic when provided in the amounts contemplated herein). Suitable active ingredients include, for example, therapeutic agents (e.g., anti-microbial agents, anti-gingivitis agents, anti-inflammatory agents, anti-caries agents, deodorizing agents, desensitizing agents, anti-calculus agents, anti-plaque agents, anti-viral agents, sealants, or remineralization agents), non-therapeutic agents (e.g., flavorants, scents, whitening agents, pigments, dyes, surfactants, abrasives, or effervescing agents such as sodium bicarbonate), oils (e.g., essential oils, flavor oils, scent oils, and oil soluble therapeutic agents such as triclosan), and combinations thereof.

Examples of suitable active ingredients include sodium fluoride, stannous fluoride, sodium monofluorophosphate, chlorhexidine, chlorhexidine salts, tetracycline, cetylpyridinium chloride, triclosan, tetrasodium pyrophosphate, disodium dihydrogen pyrophosphate, zinc chloride, zinc citrate, strontium chloride, calcium oxalate, potassium nitrate, eucalyptol, menthol, thymol, sodium lauryl sulfate, polyoxyethylene sorbitan fatty acid esters, calcium phosphates, peroxides, peppermint oil, and cinnamon. Other acceptable additives include polyacrylates, carrageenan, carboxymethyl cellulose, silica, alumina, FD&C Blue #2, and FD&C Blue #2 Lake.

The active ingredient may also include binders to provide bulk and viscosity. Examples of suitable binders include synthetic organic polymers (e.g., CARBOPOL® resins), inorganic compounds (e.g., silica powders), modified cellulose compounds (e.g., carboxymethyl cellulose and hydroxyethyl cellulose), natural vegetable gums (e.g., carrageenan and sodium alginate), and gums of bacterial origin (e.g., xanthan gum).

The preferred concentration of these substances will vary depending on the intended function of the active ingredient and can be readily determined by the artisan.

The active ingredient can be in any form that will allow it to be introduced, including solutions, dispersions, microemulsions, gels, pastes, and powders. In addition, the substance may be adsorbed onto the outer surface of microparticles applied to a surface.

Although uniform distribution of the active ingredients across the entire length and width of the textured article is often preferred, the active ingredients could also be distributed in sections or other non-uniform distributions.

Methods for Attaching Short Fibers or Texture Particles

Acid or base (e.g., formic acid, hydrochloric acid, sulfuric acid, nitric acid, acetic acid, sodium hydroxide, potassium hydroxide, ammonia, or sodium carbonate), organic solvent (e.g., ethyl acetate, acetone, chloroform, hexane, ethanol, methylene chloride, methanol, petroleum ether, diethyl ether, or acetonitrile), or heat can be used to soften the substrate material to allow the short fibers or texture particles to penetrate the surface and become physically bound to the surface after neutralization, dilution, or cooling.

In those embodiments of the invention in which the short fibers or particles are suspended in molten polymers and either used to coat the surface of a substrate or extruded as the sheath of a coaxial filament, fibers can be made from a material which has a melt temperature profile much higher than the material used in the sheath or coating, so that the small fibers retain their physical integrity. The fibers can be made of a resin capable of adhering to the sheath material such that the short fibers would be firmly anchored to the filaments produced.

To increase the mechanical integrity of the magnetic fibers or particles, a thin surface coat of a natural or synthetic coating can be applied. A surface coat would also prevent formation of rust over a prolonged period of filament wear.

PEBAX® polyetheramide materials are especially suitable for making filaments for use in the new articles and methods, since a variety of fibers can be generated with different grades of PEBAX® polyetheramide materials and the melt temperatures are relatively low (i.e., 160 to 180° C.). The melting range of the resin used as the main sheath material should ideally be relatively low since the short fibers retain their fiber characteristics. In addition, if a magnetic dipole is used to orient small fibers in the sheath of a bicomponent filament, the elevated temperature ideally should not destroy the magnetic properties associated with the material.

The fiber orientation within the sheath of an extruded bicomponent filament generally depends on a number of variables, including the speed of the extruder and the strength of the magnetic or electrical field used for orientation. As a result, the hairy filaments may not necessarily be oriented perpendicular to the main fiber but can instead be at an angle.

A procedure analogous to that used in the manufacture of pipe cleaners can also be used to produce textured articles, particularly for those embodiments in which the substrate includes filaments. In the manufacture of pipe cleaners, short fibers are fed in between two metal wires as the wires are twisted together to form a core. These fibers form the cleaning elements of the pipe cleaner. The angle and density/packing of the fibers can be controlled during the process. Additionally, other fibers can be wrapped around the product after the initial texturizing process.

Oral Brushes

Oral brushes include both toothbrushes and interdental brushes. Toothbrushes generally include a toothbrush body having a handle portion and a head portion. The head portion includes tufts of bristles, a membrane folded repeatedly to form a row of fins, or a combination of the two designs. In the new toothbrushes, short fibers or texture particles protrude from the some or all of the bristles or fins.

Interdental brushes also include a handle portion and a head portion. The head portion of an interdental brush generally includes a single rigid shaft of sufficiently small diameter to fit between the teeth. One embodiment of the present invention is a new interdental brush having short fibers or texture particles protruding from the shaft.

Smaller (i.e., 4–5 mil) filaments are capable of increased interdental penetration compared to the standard (i.e., 8 mil) filaments currently used in toothbrushes but their physical strength is compromised due their smaller diameter. Short fiber textured toothbrush filaments can enhance interdental penetration without compromising the structural integrity of the main filament shaft. In addition, short fiber filaments also result in increased surface area and a unique surface texture on each filament, which may enhance plaque removal. The addition of small fibers to the surface of floss fibers or toothbrush filaments with unique functionalities can provide an improved therapeutic effect. Referring to FIG. 1, toothbrush 10 includes a body 12 having a handle 14 and a head 16, and a bristle portion 18 attached to the head 16. Short fibers 20 protrude from the bristles 18.

Body 12 of toothbrush 10 is formed by conventional methods well-known in the art. The handle is shaped to be grasped by a hand, but alternatively can be shaped to fit into an electric toothbrush. The configuration of the head can vary and can be rectangular, oval, diamond-shaped, or any other shape. The unsecured ends of the bristles can be trimmed flat, v-shaped, serrated, convex curved, or any other desired topography. The shape and size of handle 14 and head 16 can vary and the axis of the handle and head can be on the same or a different plane. Bristle portion 18 is formed of one or more tufts of individual bristles attached to the head in manners known to the art, e.g., stapling or hot-tufting. The short fibers are attached to the bristles according to any of the methods described in the preceding section. The bristles and short fibers can be made from any of the materials described above as suitable component materials.

The bristles can have a substantially uniform cross-sectional dimension ranging from about 0.003" to about 0.15". These bristles may be cut to a desired length for use in a toothbrush. The bristles can be in the shape of a cylinder, although bristles having a variety of shapes (e.g., lobular, annular, polygonal, square, rectangular, hexagonal, diamond-shaped, keyhole-shaped, X-shaped, Y-shaped, U-shaped, or star-shaped) and configurations are also suitable. Sections of the bristle material can be bent or altered such that some of the individual sections are not in alignment with each other.

The toothbrush can include other types of bristles in combination with the textured bristles, e.g., single and multicomponent bristles (e.g., bristles formed by coextruding different polymers), crimped bristles, gum massaging bristles, bristles of varying configurations (e.g., bristles having multiple lumens), and combinations thereof. The bristles can also include a wear indicator, as described, for example, in U.S. Pat. No. 5,836,769 incorporated by reference in its entirety.

The short fiber bristles can be located in some or all of the perimeter tufts, or can be located in some or all of the interior tufts. The bristles can also be included in nonconventional tufts, in which the bristles are not fastened within a hole in the brush handle.

Figure 2:
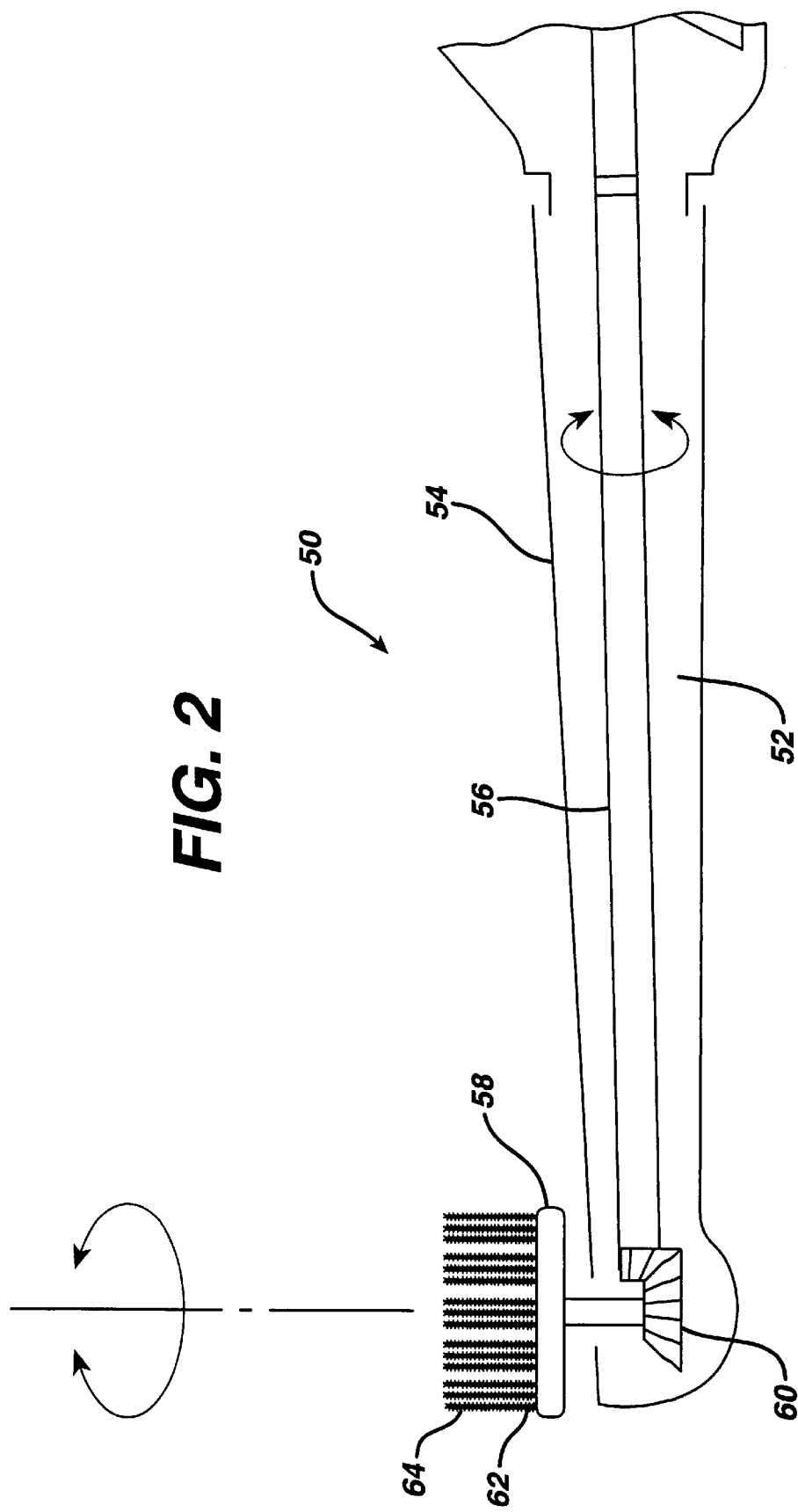
FIG. 2 is a side view of an electric toothbrush with the body cut away to reveal internal components.

The oral brush need not be a manual toothbrush having a conventional shape, as shown in FIG. 1, but can be any type of brush designed for brushing teeth that includes a body with bristles or fins extending therefrom. For example, the toothbrush can be any type of electric toothbrush, e.g., a toothbrush 50 having a body 52, a neck 54, a drive shaft 56, and a head 58 operably connected to the drive shaft 56, by a drive mechanism 60 (e.g., a pinion gear), as shown in FIG. 2. Head 58 includes a plurality of bristles 62, each having texture particles 64 on its surface.

The oral brush can be in the form of an interdental brush for brushing the interdental regions of the mouth. such an oral brush can include a single notched bristle or a number of notched bristles arranged in a single tuft, where each bristle includes short fibers.

Dental Floss

Dental floss includes any elongated flexible article used to cleanse the interdental and subgingival regions of the mouth including, for example, monofilament, multifilament and/or wax coated dental floss, or dental tape. Dental floss commonly includes a fiber core made up of one or more continuous filaments (e.g., a plurality of intertwined or braided filaments).

Materials suitable for dental floss filaments include synthetic polymer filaments (e.g., polyamides (e.g., nylon 6, nylon 6–12), rayon, polyethylene, fluoropolymers (e.g., PVDF, PTFE), PBT, acetal resins, polyester, DACRON® polyester fibers and acetate polymers, polyacrylates, polysulfones, thermoplastic elastomers, e.g., KRATON® rubbers (e.g., styrene-ethylene or styrene-butylene block copolymers), PEBAX® polyetheramide materials (e.g., polyetherpolyamide block copolymers), thermoplastic urethanes), and mixtures thereof. Such materials are preferably sufficiently strong to resist shearing or breakage under standard flossing conditions. The floss can also include a wear indicator, as described, for example, in U.S. Pat. No. 5,841,256 incorporated by reference in its entirety.

Short fiber or particle textured flosses can provide enhanced plaque removal capabilities not possible with conventional flosses. Furthermore, the surface area of a textured filament or floss can enhance the ability to deliver flavor and therapeutic agents and provide a softer, less irritating surface.

The new articles and methods are further described in the following examples, which do not limit the scope of the invention described in the claims.

EXAMPLES

Example 1

PEBAX® MX2533 resin (Elf Atochem) was placed into a glass pyrex dish and melted on a hot plate. Small diameter (0.05–0.1 mm) NICHROME® wire (Fisher) was cut into 5–10 mm segments and submerged directly into the molten PEBAX® resin. Segments cut from commercially available steel wool were also tested. While the PEBAX® resin was still molten, a magnet was held above the plastic to determine if the wire could be pulled from molten PEBAX® resin and whether the NICHROME® wire could be oriented perpendicular to the PEBAX® resin. Not only did the NICHROME® wire maintain its magnetic properties at temperatures capable of melting PEBAX® resin but it was possible to orient and pull the NICHROME® wire out of the PEBAX® resin producing on a very large scale a hairy surface concept. Clearly, wire is not acceptable for the production of toothbrush filaments; another study was thus carried out by incorporating small (i.e., micron sized) magnetic iron oxide particles within or on small fibers.

Example 2

Various types of core fibers were tested, using an acid melt procedure to attach the short fibers to the core fibers. In this procedure, both the core fibers and the short fibers were etched or softened, and then the short fibers were shot into the etched or softened core fibers (i.e., electrostatic application). Subsequent dilution of the acid produced a permanent bond. The tested core fibers included:

Nylon 6–12 8-mil

C-FLEX® elastomers (30 shore A) 90-mil

Nylon 6—6 (20 WPI crimp) 22-mil

Nylon (X-shaped) 16-mil

AMODEL® plastic monofilament (PMX 93084) 65-mil.

Each core fiber was treated with 88% formic acid for 15, 30, 45, or 60 seconds to soften the surface. Short nylon fibers 0.05", 1.8 denier (Claremont Flock, Claremont, N.H.) were electrostatically applied to the surface of the core fibers as described above, using a Dekkor B (Creative Coatings Corp. Nashua, N.H.) hand-held electrostatic flocking unit. After 1 minute the textured fibers were washed in deionized water.

In addition to texturizing fibers, sheets of various types of plastic were tested using the acid softening procedures outlined above. PEBAX® polyetheramide sheets were acid softened and successfully texturized with nylon fibers 0.05" to 0.15" in length.

Other Embodiments

It is to be understood that while the invention has been described in conjunction with the detailed description thereof, the foregoing description is intended to illustrate and not limit the scope of the invention, which is defined by the scope of the appended claims. The materials, methods, and examples described herein are illustrative only and not intended to be limiting. Other aspects, advantages, and modifications are within the scope of the following claims.

What is claimed is:

1. A method for manufacturing a textured toothbrush bristle, comprising:

softening an end of fibers having two ends;

softening a part of a surface of a toothbrush bristle, wherein the toothbrush bristle has a cross-sectional dimension of about 0.003" to about 0.008";

contacting the softened end of the fibers and the softened toothbrush bristle surface; and hardening the softened fibers and bristle to produce said textured toothbrush bristle.

2. The method of claim 1, wherein said part of the surface of the toothbrush bristle is softened by treating the surface with a solvent.

3. The method of claim 1, wherein the end of the fibers that contacts the toothbrush bristle surface is softened by treating the fibers with a solvent.

4. The method of claim 1, further comprising supplying an electrostatic field, thereby causing the fibers to align at a substantially fixed angle relative to the surface of the bristle.

5. The method of claim 4, wherein, prior to softening, the fibers are coated with an electrically conductive material.

6. The method of claim 1, wherein the fibers have a length of from about 0.03" to 0.25".

7. The method of claim 1, wherein the fibers have a diameter of from about 0.004" to 0.1".

8. The method of claim 1 further comprising arranging the fibers in a pattern during the contacting step.

9. The method of claim 1 further comprising, prior to softening, treating the fibers with an active ingredient.

10. The method of claim 1 wherein the fibers comprise a biodegradable material and an active ingredient incorporated into the biodegradable material.

11. The method of claim 1 wherein the fibers comprise a water-soluble material and an active ingredient incorporated into the water-soluble material.

12. A method for manufacturing a textured toothbrush bristle, comprising:

coating fibers with an electrically conductive material, the fibers having two ends;

softening an end of the fibers;

softening a part of a surface of a toothbrush bristle;

contacting the softened end of the fibers and the softened toothbrush bristle surface; and hardening the softened fibers and bristle to produce said textured toothbrush bristle.

* * * * *

UNITED STATES PATENT AND TRADEMARK OFFICE
CERTIFICATE OF CORRECTION

PATENT NO. : 6,475,553 B2  Page 1 of 1
DATED : November 5, 2002
INVENTOR(S) : Norbert Schaefer et al.

It is certified that error appears in the above-identified patent and that said Letters Patent is hereby corrected as shown below:

Title page,
Item [56], U.S. PATENT DOCUMENTS, delete "3,743,557 A  7/1973  Grohmannetal" and insert -- 3,743,557 A  9/1990  Grohmannetal --.
Delete "3,775,233 A  11/1973  Malge" and insert -- 3,775,233 A  11/1993  Malge --.
Delete "3,922,410 A  11/1975  Halloran" and insert -- 3,922,410 A  11/1973  Halloran --.
Delete "4,671,980 A  6/1987  Goerens" and insert -- 4,671,980 A  11/1987  Goerens --

Signed and Sealed this

Twenty-fifth Day of March, 2003

JAMES E. ROGAN
*Director of the United States Patent and Trademark Office*